(12) United States Patent
Spangler et al.

(10) Patent No.: US 10,893,882 B2
(45) Date of Patent: Jan. 19, 2021

(54) ATHERECTOMY MOTOR CONTROL SYSTEM WITH TACTILE FEEDBACK

(71) Applicant: BOSTON SCIENTIFIC SCIMED, INC., Maple Grove, MN (US)

(72) Inventors: David Gordon Spangler, New Richmond, WI (US); Corydon Carlson, Stillwater, MN (US); Laszlo Trent Farago, Hudson, WI (US); Daniel Frank Massimini, Brooklyn Park, MN (US); Mark A. Hilse, Ham Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 144 days.

(21) Appl. No.: 16/286,252

(22) Filed: Feb. 26, 2019

(65) Prior Publication Data

US 2019/0262022 A1 Aug. 29, 2019

Related U.S. Application Data

(60) Provisional application No. 62/636,113, filed on Feb. 27, 2018.

(51) Int. Cl.
*A61B 17/32* (2006.01)
*A61B 90/00* (2016.01)
(Continued)

(52) U.S. Cl.
CPC ............ *A61B 17/32002* (2013.01); *A61B 17/320758* (2013.01); *A61B 34/76* (2016.02);
(Continued)

(58) Field of Classification Search
CPC .......... A61B 17/32002; A61B 17/3207; A61B 17/320725; A61B 17/320758;
(Continued)

(56) References Cited

U.S. PATENT DOCUMENTS

| 10,736,628 B2 * | 8/2020 | Yates ................. A61B 17/3205 |
| 2002/0058956 A1 * | 5/2002 | Honeycutt ...... A61B 17/320758 |
| | | 606/159 |

(Continued)

FOREIGN PATENT DOCUMENTS

| EP | 2053534 A1 | 8/2013 |
| EP | 3192461 A1 | 8/2014 |

OTHER PUBLICATIONS

International Search Report and Written Opinion dated Apr. 26, 2019, for International Application No. PCT/US2019/019631.

*Primary Examiner* — Katherine H Schwiker
*Assistant Examiner* — Alexis D Amechi
(74) *Attorney, Agent, or Firm* — Seager, Tufte & Wickhem, LLP

(57) ABSTRACT

An atherectomy system includes a handle and a drive motor that is adapted to rotate a drive cable extending through the handle and operably coupled to an atherectomy burr. A control system is adapted to regulate operation of the drive motor, including providing the drive motor with a high frequency pulse width modulation (PWM) drive signal in order to operate the drive motor. The control system monitors a motor performance parameter such as motor speed or motor torque, and when the motor performance parameter approaches a limit of a performance range, the control system adds a low frequency PWM signal to the high frequency PWM drive signal, thereby causing the drive motor to produce a tactile signal that signals to the user that the motor performance parameter is approaching the limit of the performance range.

20 Claims, 7 Drawing Sheets

(51) Int. Cl.
*A61B 17/3207* (2006.01)
*A61B 34/00* (2016.01)
*G05B 11/28* (2006.01)
*A61B 17/00* (2006.01)
*A61B 18/00* (2006.01)

(52) U.S. Cl.
CPC .............. *A61B 90/06* (2016.02); *G05B 11/28* (2013.01); *A61B 2017/003* (2013.01); *A61B 2017/00017* (2013.01); *A61B 2017/00022* (2013.01); *A61B 2017/00119* (2013.01); *A61B 2017/00398* (2013.01); *A61B 2017/320741* (2013.01); *A61B 2018/00303* (2013.01); *A61B 2090/064* (2016.02); *A61B 2090/066* (2016.02); *A61B 2090/08021* (2016.02); *A61B 2217/005* (2013.01); *A61B 2217/007* (2013.01)

(58) Field of Classification Search
CPC ................ A61B 2017/320024–320032; A61B 2017/320004; A61B 2017/320766; A61B 2017/320775; A61B 2017/00115–00128
See application file for complete search history.

(56) References Cited

U.S. PATENT DOCUMENTS

| | | | |
|---|---|---|---|
| 2007/0239140 A1* | 10/2007 | Chechelski | A61M 25/0105 606/1 |
| 2013/0253552 A1* | 9/2013 | Schoenle | G06F 13/10 606/159 |
| 2014/0222042 A1* | 8/2014 | Kessler | A61B 17/320783 606/159 |
| 2017/0181760 A1* | 6/2017 | Look | A61M 1/0031 |

\* cited by examiner

ATHERECTOMY MOTOR CONTROL SYSTEM WITH TACTILE FEEDBACK

CROSS-REFERENCE TO RELATED APPLICATIONS

This application claims the benefit of priority under 35 U.S.C. § 119 of U.S. Provisional Application No. 62/636,113, filed Feb. 27, 2018, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, the disclosure is directed to an atherectomy device system that includes a handle and a drive motor that is adapted to rotate a drive cable extending through the handle and operably coupled to an atherectomy burr. A control system is adapted to regulate operation of the drive motor and is further adapted to provide the drive motor with a high frequency pulse width modulation (PWM) drive signal in order to operate the drive motor and monitor a motor performance parameter. When the motor performance parameter approaches a limit of a performance range, the control system adds a low frequency PWM signal to the high frequency PWM drive signal, thereby causing the drive motor to produce a tactile signal that signals to the user that the motor performance parameter is approaching the limit of the performance range.

Alternatively or additionally, when the motor performance parameter crosses the limit of the performance range, the control system may change a frequency and/or amplitude of the low frequency PWM signal in order to make the tactile signal more noticeable.

Alternatively or additionally, when the motor performance parameter exceeds the limit of the performance range by a predetermined amount, the control system may further change the frequency and/or amplitude of the low frequency PWM signal in order to further increase an intensity of the tactile signal.

Alternatively or additionally, the tactile signal may include a vibration detectable in the handle by an operator of the atherectomy system.

Alternatively or additionally, the tactile signal may further include an audible buzz detectable by an operator of the atherectomy system.

Alternatively or additionally, the motor performance parameter may include a motor torque, and the control system may be adapted to add the low frequency PWM signal to the high frequency PWM drive signal in response to the motor torque approaching or exceeding a predetermined torque value.

Alternatively or additionally, the motor performance parameter may include a motor speed, and the control system may be adapted to add the low frequency PWM signal to the high frequency PWM drive signal in response to the motor speed approaching or dropping below a predetermined speed value.

Another example of the disclosure is an atherectomy system that includes a drive motor that is adapted to rotate a drive cable operably coupled to an atherectomy burr and a control system that is adapted to regulate operation of the drive motor. The control system is further adapted to provide the drive motor with a high frequency pulse width modulation (PWM) drive signal in order to operate the drive motor. The control system monitors a torque exerted by the drive motor as well as a speed of the drive motor. When the torque approaches a torque threshold and/or when the speed approaches a speed threshold, the control system adds a low frequency PWM signal to the high frequency PWM drive signal, thereby causing the drive motor to produce a tactile signal that signals to the user that the torque is approaching the torque threshold and/or the motor speed is approaching the speed threshold.

Alternatively or additionally, when the torque passes the torque threshold, the control system may change the amplitude and/or frequency of the low frequency PWM signal being added to the high frequency PWM drive signal in order to increase an intensity of the tactile signal in order to signal to the user that the torque is passing the torque threshold.

Alternatively or additionally, when the speed passes the speed threshold, the control system may change the amplitude and/or frequency of the low frequency PWM signal being added to the high frequency PWM drive signal in order to increase an intensity of the tactile signal in order to signal to the user that the speed is passing the speed threshold.

Alternatively or additionally, the control system may be further adapted to alter a frequency and/or a magnitude of the low frequency PWM signal in response to how high the torque is relative to the torque threshold and/or how low the speed of the motor is relative to the speed threshold.

Alternatively or additionally, the control system may be further adapted to maintain a safe level of torque at the atherectomy burr.

Alternatively or additionally, the control system may be further adapted to maintain an effective speed at the atherectomy burr.

Another example of the disclosure is a control system for an atherectomy system that includes a drive motor adapted to rotate a drive cable operably coupled to an atherectomy burr. The control system includes an input that is adapted to receive an indication of a motor performance parameter, an output that is adapted to output a high frequency pulse width modulation (PWM) drive motor signal to the drive motor and a controller that is operably coupled to the input and to the output, the controller adapted to provide to the output the high frequency PWM signal for operating the drive motor. The controller is further adapted, when the motor performance parameter approaches a limit of a performance range, to add a low frequency PWM signal to the high frequency PWM drive signal that is provided to the drive motor via the output, thereby causing the drive motor to produce a tactile signal that signals to the user that the motor performance parameter is approaching the limit of the performance range.

Alternatively or additionally, the motor performance parameter may include motor torque.

Alternatively or additionally, when the motor torque passes a torque threshold, the controller may change an amplitude and/or a frequency of the low frequency PWM signal being added to the high frequency PWM drive signal in order to increase an intensity of the tactile signal in order to signal to the user that the torque is passing the torque threshold.

Alternatively or additionally, the controller may be further adapted to further alter the amplitude and/or the frequency of the low frequency PWM signal in response to how high the torque is relative to the torque threshold.

Alternatively or additionally, the motor performance parameter may include motor speed.

Alternatively or additionally, when the motor speed passes a motor speed threshold, the controller may change an amplitude and/or a frequency of the low frequency PWM signal being added to the high frequency PWM drive signal in order to increase an intensity of the tactile signal in order to signal to the user that the motor speed is passing the motor speed threshold.

Alternatively or additionally, the controller may be further adapted to further alter the frequency and/or the magnitude of the low frequency PWM signal in response to how high the torque is relative to the torque threshold and/or how low the speed of the motor is relative to the speed threshold.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
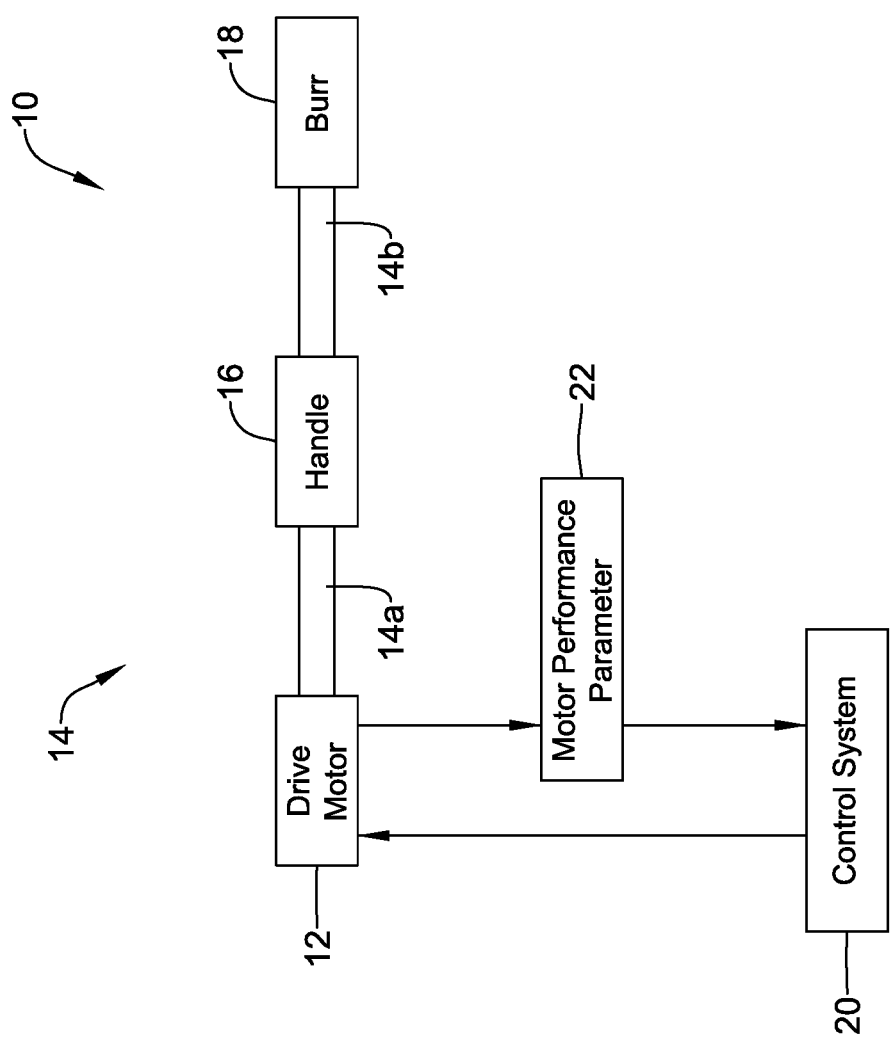
FIG. 1 is a schematic block diagram of an example atherectomy system including a control system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 is a schematic block diagram of an example atherectomy system 10. The atherectomy system 10 includes a drive motor 12 that is operably coupled to a drive cable 14 such that actuation of the drive motor 12 causes the drive cable 14 to rotate. The drive cable 14 includes a first section 14a that is proximal to a handle 16 and a second section 14b that is distal to the handle 16. The drive cable 14 may pass through the handle 16, for example, and extends distally to an atherectomy burr 18. In some cases, the atherectomy burr 18 may also be referred to as being or including a cutting head or a cutting member, and these terms may be used interchangeably. Accordingly, actuation of the drive motor 12 causes the drive cable 14 to rotate, which in turn causes the atherectomy burr 18 to rotate. In some cases, the atherectomy system 10 may include additional components not illustrated, such as but not limited to suction or vacuum systems, fluid sources, and the like.

In some cases, the atherectomy system 10 may include a control system 20. The control system 20 may be adapted, for example, to control operation of the drive motor 12. In some instances, control of the drive motor 12 may simply include turning the drive motor 12 on and/or off. In some cases, the control system 20 may be adapted to regulate a motor speed of the drive motor 12. The control system 20 may be adapted to monitor operation of the drive motor 12. In some cases, for example, the control system 20 may monitor a motor performance parameter 22. The motor performance parameter 22 may provide an indication of how well the drive motor 12 is working, or perhaps an indication of how hard the drive motor 12 is working. The motor performance parameter 22 may, for example, include or be representative of a motor torque exerted by the drive motor 12. The motor performance parameter 22 may, for example, include or be representative of a motor speed achieved by the drive motor 12. In some cases, the motor performance parameter 22 may include one or more of axial force, torque, voltage, current, speed, acceleration and deceleration.

In operation of the atherectomy system 10, there may be a desire to maintain the speed of the atherectomy burr 18, and thus the drive motor 12, within a particular safe operating range. For example, a suitable safe operating range may require a motor speed that is in the range of 0 to about 250,000 RPM. In some cases, there may be a desire to maintain a torque exerted on the atherectomy burr 18 within a safe range. If the torque is too low, the atherectomy burr 18 may not be rotating fast enough to be efficient, or may not be encountering any resistance. This could occur, for example, if the atherectomy burr 18 has not been advanced sufficiently, and is simply spinning within a blood vessel without contacting an occlusion. Conversely, if the torque is too high, this may be an indication that the atherectomy burr 18 is stuck, or has otherwise contacted an occlusion it is unable to burr through.

In some cases, if the motor speed is outside a predetermined speed range, or if the torque is outside a predetermined torque range, it may be useful to communicate this information to the individual running the atherectomy system 10. In some instances, it may be useful to communicate this information in such a way as to inform the individual running the atherectomy system 10 without requiring the individual to look at a control panel, or otherwise look up from what they are doing. In some cases, the atherectomy system 10 is adapted to permit the control system 20 to modify a drive signal being provided to the drive motor 12 that will cause the drive motor 12 to vibrate and/or cause an audible sound. As a result, the individual is informed that either speed or torque are outside of their predetermined desirable ranges. In some cases, the control system 20 is adapted to provide a high frequency pulse width modulation (PWM) drive signal to the drive motor 12. The high frequency PWM drive signal causes the drive motor 12 to operate smoothly at a desired (unloaded) speed, which of course decreases under load. In some cases, the high frequency PWM drive signal may have a frequency that varies in accordance with motor construction and speed of operation, among other factors. In some cases, the high frequency PWM drive signal may have a frequency as high as 100 KHz.

In some cases, the control system 20 is adapted to add a low frequency PWM signal to the high frequency PWM drive signal. While the low frequency PWM signal does not materially change the motor speed of the drive motor 12, and does not materially change the torque provided by the drive motor 12, the addition of the low frequency PWM signal may cause the drive motor 12 to vibrate and/or create an audible noise. In some cases, the low frequency PWM drive signal may have a frequency that is in the range of about 0 to 5 KHz. If the control system 20 introduces the low frequency PWM signal in response to the motor performance parameter 22 being found to be outside of a desirable range, for example, the individual may be made aware that the motor performance parameter 22 is outside of a desirable range for that parameter.

The control system 20 monitors the motor performance parameter 22, which as noted may for example be the motor speed of the drive motor 12, or the torque being exerted by the drive motor 12. In some cases, when the motor performance parameter 22 approaches a limit of a performance range, the control system 20 adds a low frequency PWM signal to the high frequency PWM drive signal, thereby causing the drive motor 12 to produce a tactile signal that signals to the user that the motor performance parameter is approaching the limit of the performance range. A tactile signal may be a vibration, an audible noise or a combination thereof. In some cases, the tactile signal may be a vibration that is detectable in the handle 16 by the operator of the atherectomy system 10. In some instances, the tactile signal may include an audible buzz that is detectable by the operator of the atherectomy system 10.

In some cases, when the motor performance parameter actually crosses the limit of the performance range, the control system 20 may change a frequency and/or amplitude of the low frequency PWM signal in order to make the tactile signal more noticeable. This may, for example, serve as a warning to the individual operating the atherectomy system 10. In some cases, if the individual operating the atherectomy system 10 does not back off, and the motor performance parameter 22 exceeds the limit of the performance range by a predetermined amount, the control system 20 may further change the frequency and/or amplitude of the low frequency PWM signal in order to further increase an intensity of the tactile signal and thus make the tactile signal more noticeable.

In some cases, the motor performance parameter 22 includes a motor torque, and the control system 20 may be adapted to add the low frequency PWM signal to the high frequency PWM drive signal in response to the motor torque approaching or exceeding a predetermined torque value. In some cases, the motor performance parameter 22 includes a motor speed, and the control system 20 may be adapted to add the low frequency PWM signal to the high frequency PWM drive signal in response to the motor speed approaching or dropping below a predetermined speed value.

Figure 2:
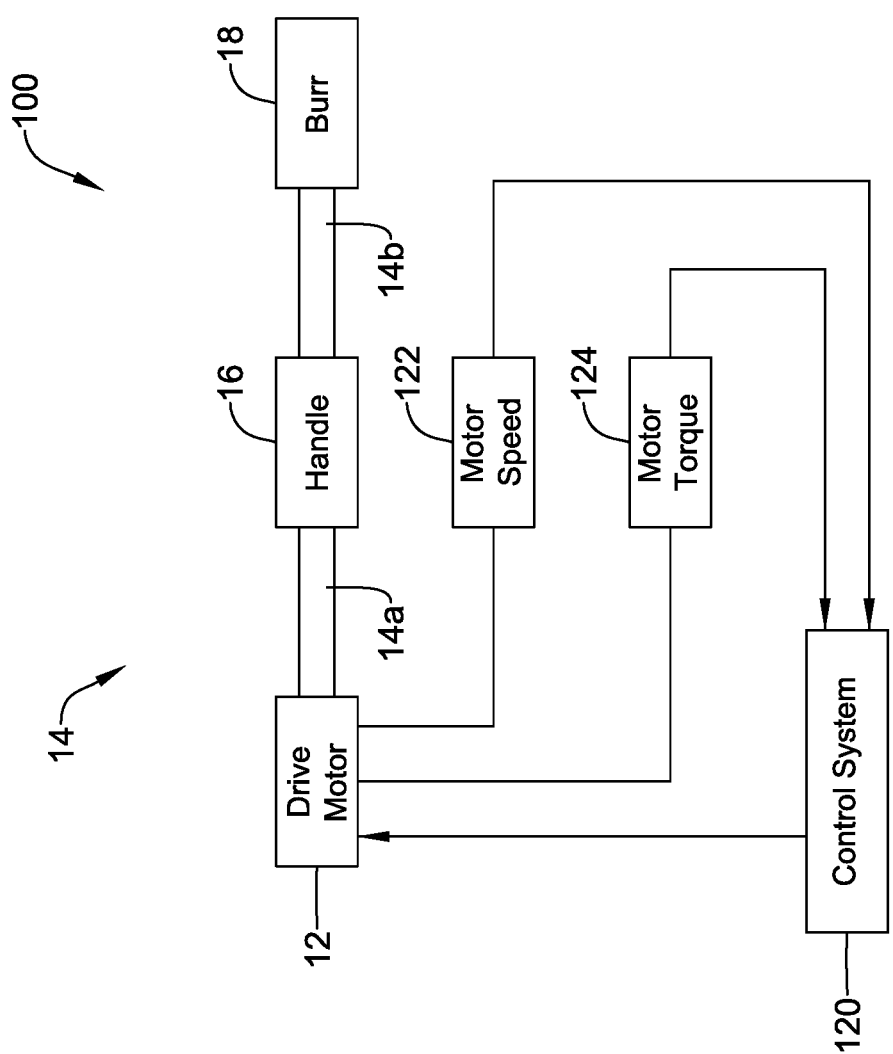
FIG. 2 is a schematic block diagram of an example atherectomy system including a control system.

FIG. 2 is a schematic block diagram of an example atherectomy system 100 that is similar to the atherectomy system 10 shown in FIG. 1, but the atherectomy system 100 includes a control system 120. The control system 120 may be adapted to control operation of the drive motor 12. It will be appreciated that features of the atherectomy system 10 may be included in the atherectomy system 100, and vice versa. The control system 120 is adapted to provide the drive motor 12 with a high frequency pulse width modulation (PWM) drive signal in order to operate the drive motor 12. In some cases, the control system 120 is adapted to monitor a motor speed 122 of the drive motor 12 as well as a motor torque 124 of the drive motor 12. When the torque approaches a torque threshold and/or when the speed approaches a speed threshold, the control system 120 may add a low frequency PWM signal to the high frequency PWM drive signal, thereby causing the drive motor 12 to produce an audible vibration that signals to the user that the torque is approaching the torque threshold and/or the motor speed is approaching the speed threshold.

In some cases, the control system 120 is further adapted to maintain a safe level of torque at the atherectomy burr 18. In some instances, the control system 120 is further adapted to maintain an effective speed at the atherectomy burr 18. In some cases, a suitable torque range is between 0 and about 250,000 RPM. A suitable torque range may be 0 to about 5 inch-ounces.

In some cases, when the speed 122 decreases below or increases above the speed threshold, the control system 120 may change the amplitude and/or frequency of the low frequency PWM signal being added to the high frequency PWM drive signal in order to increase the audible vibration to signal to the user that the speed is passing the speed threshold. In some cases, when the motor torque 124 passes the torque threshold, the control system 120 may change the amplitude and/or the frequency of the low frequency PWM signal being added to the high frequency PWM drive signal in order to increase the audible vibration to signal to the user that the torque is passing the torque threshold. In some cases, the control system 120 may be further adapted to further alter the frequency and/or the magnitude of the low frequency PWM signal in response to how high the torque is relative to the torque threshold and/or how low the speed of the motor is relative to the speed threshold. In some cases, the frequency of the low PWM signal may vary from 0 to about 5 KHz and the amplitude of the low PWM signal may vary from 0 to 100 percent of the control drive signal.

Figure 3:
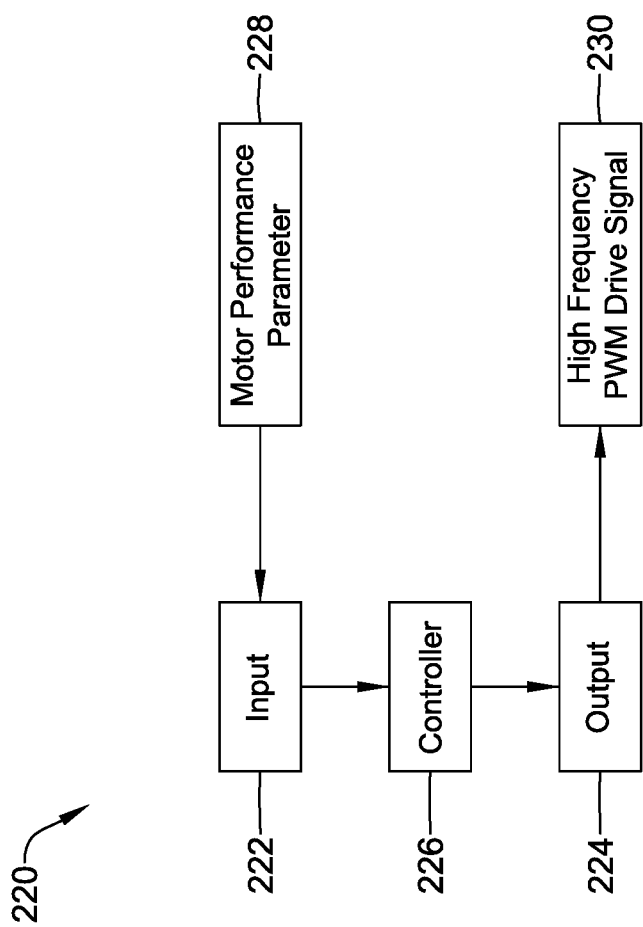
FIG. 3 is a schematic block diagram of an example control system useful in the example atherectomy systems of FIG. 1 and FIG. 2.

FIG. 3 is a schematic block diagram of a control system 220 for an atherectomy system (such as the atherectomy system 10 shown in FIG. 1 or the atherectomy system 110 shown in FIG. 2). In some cases, the control system 220 may be considered as being an example of the control system 20 or the control system 120, and features of the control system 220 may be combined with features of the control system 20 and/or the control system 120, for example. The control system 220 includes an input 222, an output 224 and a controller 226 that is operably coupled to the input 222 and to the output 224. In some cases, the input 222 is adapted to receive an indication of a motor performance parameter 228 and the output 224 may be adapted to output a high frequency pulse width modulation (PWM) drive motor signal 230 to the drive motor. The controller 226 may be adapted to provide the high frequency PWM drive motor signal to the output 224. In some cases, the controller 226 may be further adapted, when the motor performance parameter approaches a limit of a performance range, to add a low frequency PWM signal to the high frequency PWM drive signal 230 that is provided to the drive motor via the output, thereby causing the drive motor to produce a tactile signal that signals to the user that the motor performance parameter is approaching the limit of the performance range.

In some cases, the motor performance parameter 228 includes motor torque. When the motor torque passes a torque threshold, the controller 226 may change an amplitude and/or a frequency of the low frequency PWM signal being added to the high frequency PWM drive signal in order to increase the tactile signal in order to signal to the user that the torque is passing the torque threshold. In some cases, the controller 226 may be further adapted to further alter the frequency and/or amplitude of the low frequency PWM signal in response to how high the torque is relative to the torque threshold.

In some cases, the motor performance parameter 228 may include motor speed. When the motor speed passes a motor speed threshold, the controller 226 may change an amplitude and/or a frequency of the low frequency PWM signal being added to the high frequency PWM drive signal 230 in order to increase the tactile signal in order to signal to the user that the motor speed is passing the motor speed threshold. In some cases, the controller 226 may be further adapted to further alter the frequency and/or the magnitude of the low frequency PWM signal in response to how high the torque is relative to the torque threshold and/or how low the speed of the motor is relative to the speed threshold.

Figure 4:
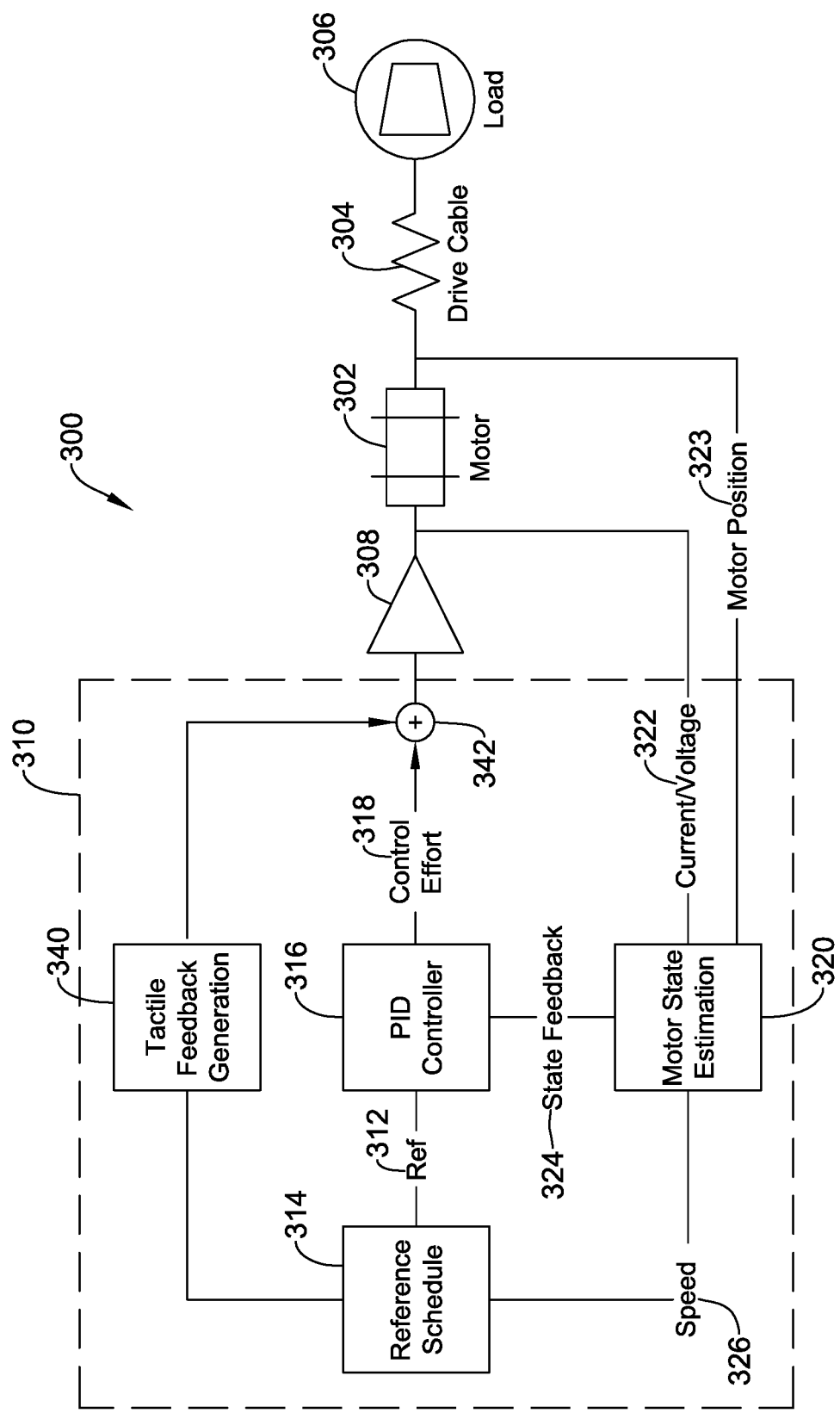
FIG. 4 is a schematic block diagram of an example atherectomy system

FIG. 4 is a schematic block diagram of an example atherectomy system 300. In some cases, the atherectomy system 300 may be considered as being an example of the atherectomy system 10 (FIG. 1) or the atherectomy system 100 (FIG. 2). In some instances, features of the atherectomy system 300 may be combined with features of the atherectomy system 10 and/or the atherectomy system 100, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the control system 20, the control system 120 and/or the control system 220.

The drive circuitry 308 receives an input from a feedback portion 310. In some cases, the feedback portion 310 begins with a reference input 312 from a reference schedule block 314, which provides the reference input 312 to a PID controller 316. A PID controller is a controller that includes a (P) proportional portion, an (I) integral portion and a (D) derivative portion. In some cases, the reference schedule block 314 may be configured to accept additional inputs, such as from a user and/or from additional sensors not illustrated. As an example, if the device has been running for too long of a period of time, the reference schedule block 314 may reduce the speed reference in order to prevent overheating. The PID controller 316 outputs a control effort value 318 to a summation point 342. In some cases, a tactile feedback generation block 340 will output a low frequency pulse width (PWM) signal that is added to the control effort value 318 at the summation point 342. The result is then output to the drive circuitry 308. A motor state estimation block 320 receives a current/voltage signal 322 and a motor position signal 323 from the drive circuitry 308 and receives state feedback 324 from the PID controller 316. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed. The motor state estimation block 320 outputs a speed value 326 back to the reference schedule block 314, although in some cases this may be a position reference instead.

Figure 5:
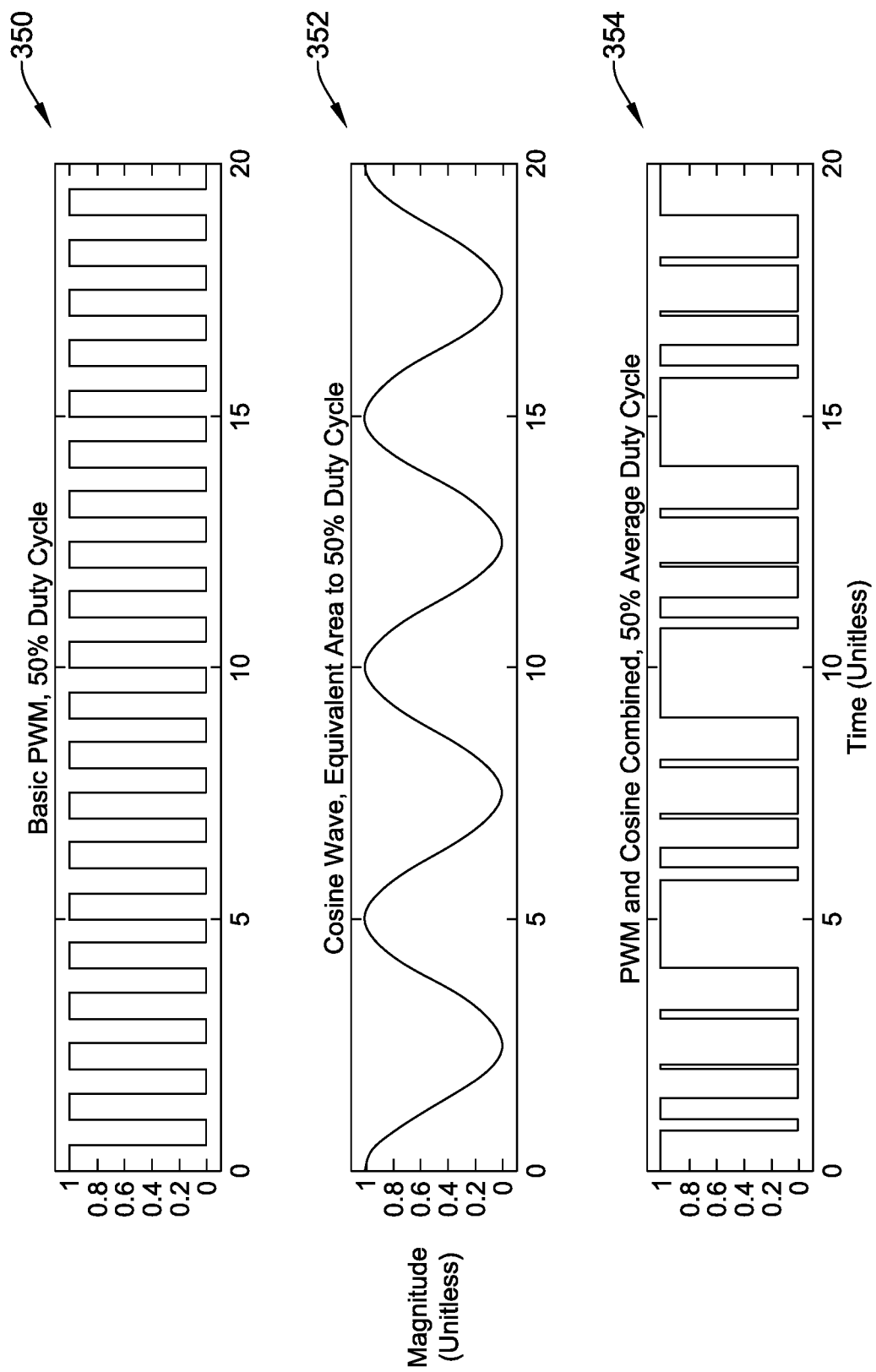
FIG. 5 is a graphical representation of a high frequency pulse width modulation (PWM) drive signal combined with a low frequency PWM signal as may be output by the control systems of FIGS. 1-4.

FIG. 5 is a graphical representation of a high frequency pulse width modulation (PWM) drive signal combined with a low frequency PWM signal. It will be appreciated that the graphs shown in FIG. 5 are merely illustrative and are not intended to be limiting in any fashion. The first plot 350, at the top of FIG. 5, shows an example high frequency PWM signal. The plot 350 represents a basic 50% duty cycle signal, which is merely illustrative. The middle plot 352 shows an example low frequency PWM signal. While the middle plot 352 illustrates a sinusoidal wave, other wave forms are contemplated, such as but not limited to square wave, sawtooth wave or any arbitrary repeating wave pattern. In some cases, as illustrated, the middle plot 352 has an equivalent area to that shown in the top plot 350, meaning that the net control of the drive motor is largely unaffected. The bottom plot 354 represents the summation of the top plot 350, showing the high frequency PWM signal, and the middle plot 352, showing the low frequency PWM signal. It should be noted that the differences in frequency between the high frequency PWM signal and the low frequency PWM signal being added to the high frequency PWM signal will generally be much larger than what is illustrated.

Figure 6:
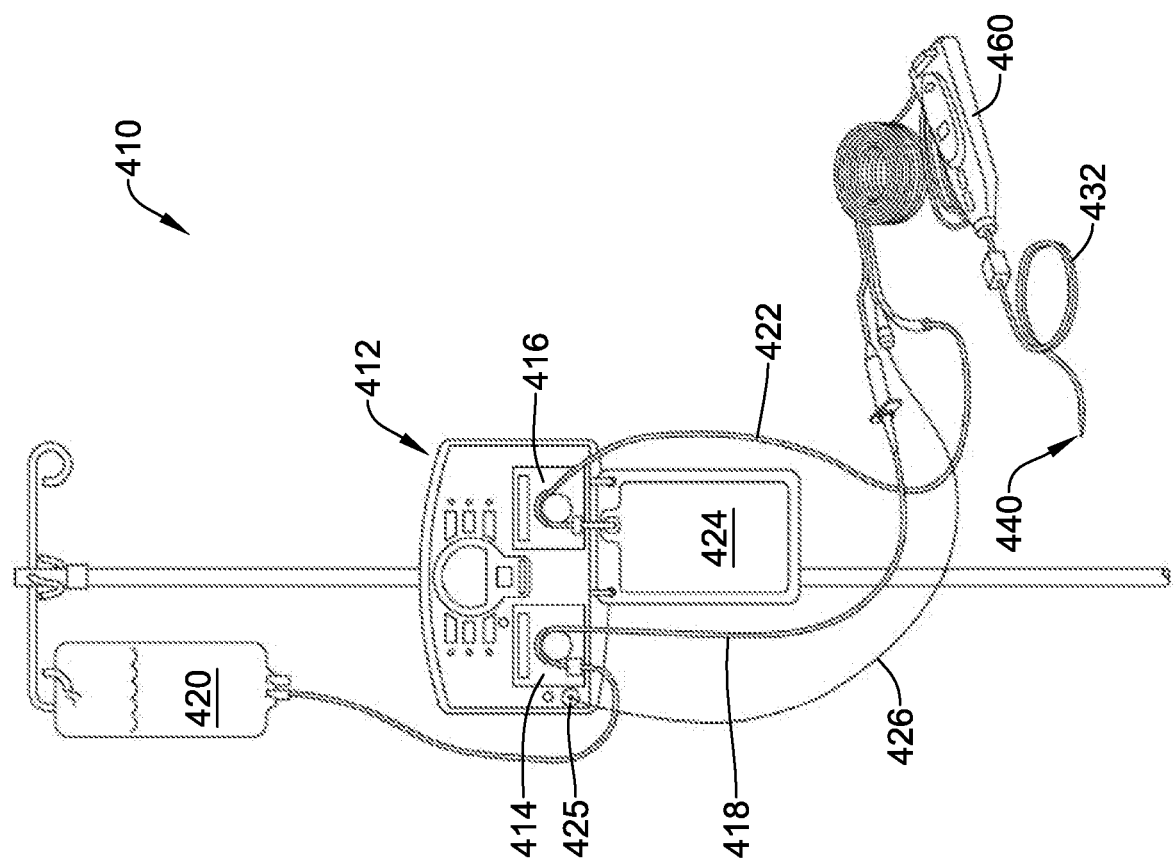
FIG. 6 is a schematic diagram of an example atherectomy system that may utilize the atherectomy control systems referenced in FIG. 1 through FIG. 4.

FIG. 6 illustrates an exemplary example of an interventional catheter assembly 410 with which the atherectomy systems 10, 100, 300, and the control systems 20, 120, 220 described therein, may be used. The interventional catheter assembly 410 includes a console unit 412, a controller 460, and a catheter system 432 having an operating head 440 located at or in proximity to the distal end of the catheter system. The controller 460 may be used to manipulate (e.g. advance and/or rotate) the catheter system 432 and operating head 440, or alternative controls may be provided. In some cases, some or all of the functionality of the controller 460 and/or the console unit 412 may be built into the atherectomy systems 10, 100, 300 and/or the control systems 20, 120, 220.

The console unit 412 incorporates an infusion pump 414 and an aspiration pump 416. During operation of the interventional catheter, an infusate conduit 418 draws fluid from an infusate reservoir 420 and operably contacts the infusion pump 414 to provide fluid through an infusion lumen in catheter system 432 to one or more infusion ports provided in proximity to the operating head. Similarly but in reverse, fluids with entrained particulates are withdrawn from the site of intervention through an aspiration lumen in the catheter system 432 and conveyed to an aspiration conduit 422, which is in operable contact with the aspiration pump 416, and communicates with the aspirate collection vessel 424. The console unit 412 may also provide a power source for operating the operating head and system components, or it may be in communication with an external power source. In some cases, the console unit 412 may provide power to the interventional catheter assembly and the controller 460 via a device power port 425 and power cord 426.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 412. The console unit 412 is generally provided as a reusable assembly and is generally operated outside the sterile field. It may be mountable on a portable stand to facilitate convenient placement during interventions.

One function of the console unit 412 is to provide feedback of system and/or environmental conditions or operating parameters. The console unit may output operational information concerning operating conditions and feedback from the material removal site to the operator. In some cases, the console unit 412 may provide continuously updated output to an operator of operating parameters such as operating head rotation rate, which may include the actual run speed as well as the desired speed; operating head advance rate; aspiration rate and/or volume; infusion rate and/or volume; length of the body or matter to be removed that is traversed; and the like.

Certain automated and selectable control features may be implemented in the console unit 412. Preset routines or programs involving various operating parameters may be preselected, stored and selectable by an operator, for example. Thus, in some cases, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as: cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

In some cases, aspiration may be included. In certain cases, fluid and associated particulates are aspirated from the intervention site at rates of at least 5 ml/min and, in many cases, fluid and associated particulates are aspirated at rates of at least 15 ml/min or at least 25 ml/min. In exemplary interventional catheter systems, the aspiration site may be more than a meter away from the controller 460 through an aspirate removal passageway located within the catheter system 432 and having a diameter of less than 0.10 inch, for example between about 0.050 to 0.070 inch. The distance that the aspirate travels between controller 460 and console unit 412 may be from about ½ meter to several meters, through an aspirate conduit that is between about 0.015 to about 1.0 inch in diameter. The blood and debris being aspirated are relatively viscous fluids, and achieving a relatively constant and high level of aspiration under these conditions is essential.

In one case, aspiration pump 416 may be a multi-lobed roller pump. The rotation rates of multiple rollers, or of a multi-lobed rotating structure, may be variable or selectable to control the aspiration rate and volume. Roller pumps permit fluid to flow in a conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. For example, a collection bag 424 and a sealed aspiration conduit may be provided as part of a sterile disposable interventional catheter kit. A distal end of the aspiration conduit may be pre-mounted on and sealed to the controller 460. A proximal portion of the aspiration conduit is mounted on the aspiration pump prior to operation of the interventional catheter and the aspirate collection bag is mounted to or in proximity to the control module.

The infusion pump 414 may also be a multi-lobed roller pump employing variable or selectable rotation rates to control the infusion rate and volume. A simple bag or another infusate reservoir, such as those used for intravenous infusions, may be used to supply the infusate. For example, an infusate reservoir 420 having a sealed conduit that is mounted in the infusion pump 416 during operation of the interventional catheter may be provided. In some cases, the sealed infusate conduit may be provided as part of the sterile disposable interventional catheter system and a distal end of the infusate conduit may be pre-mounted on and sealed to the controller 460. A proximal portion of the infusate conduit may be connected to an infusate reservoir, such as a saline bag, and mounted in proximity to the infusion pump prior to operation. A control feature that automatically disables the infusion pump and/or power to the operating head may be activated upon detection of a fault (e.g. a bubble) in the infusate conduit.

The console unit 412 may also have control switches for activating and shutting down the aspiration pump and system, and for activating and shutting down the infusion pump and system. These control features may be provided as simple on/off switches. Alternatively, systems providing different levels or rates of aspiration and/or infusion that are selectable by an operator may be provided. In addition, the console unit 412 may be provided with a timing mechanism that determines, and displays, the elapsed time of operation of the operating head and/or the aspiration and infusion systems. The volumes of aspirate withdrawn and the volume of infusate introduced may also be detected and displayed by the console unit 412. Detection systems for monitoring the levels of aspirate and infusate in the respective reservoirs may be incorporated and alarms indicating an overfill condition for the aspirate collection system or a low supply condition for the infusate reservoir may be provided. Backup aspirate collection and infusate supply systems may also be provided.

In some cases, the console unit 412, together with the aspiration pump 416, the infusion pump 414 and the associated control and display features, may be provided as a separate, re-usable unit, that may be used as standard equipment in operating rooms, for example. In the system illustrated, the console unit 412 is not contaminated by contact with blood or aspirate during operation, and the power and control systems are durable and long-lasting and may be reused for many interventions. The console unit 412 may be provided in a housing designed to sit on a platform during operation, or the housing may be designed for mounting on a portable structure, such as an i.v. pole or another structure, or may be a self-contained free-standing portable structure. The interventional catheter system, including the catheter system 432 with the operating head 440, the controller 460, the aspirate conduit 422, the aspirate collection vessel 424, and the infusate conduit 418 may be provided as a sterile, single use system kit.

The controller 460, which may be constructed from a durable, sterilizable material, such as hard plastic, may be provided in any convenient ergonomic design and constructed for placement in proximity to and/or in contact with the external body. In one instance, the controller may include an integrated handle for operator convenience in holding and supporting the controller during operation. The catheter system 432, exiting the controller 460, may be axially translatable with respect to the controller 460 as the operating head and catheter system are guided to a target material removal site. It will be appreciated that some of the control and operational features described herein with reference to the controller 460 may be provided in the console unit 412 and, likewise, some of the control and operational features described with reference to the console unit 412 may be provided in the controller 460.

Figure 7:
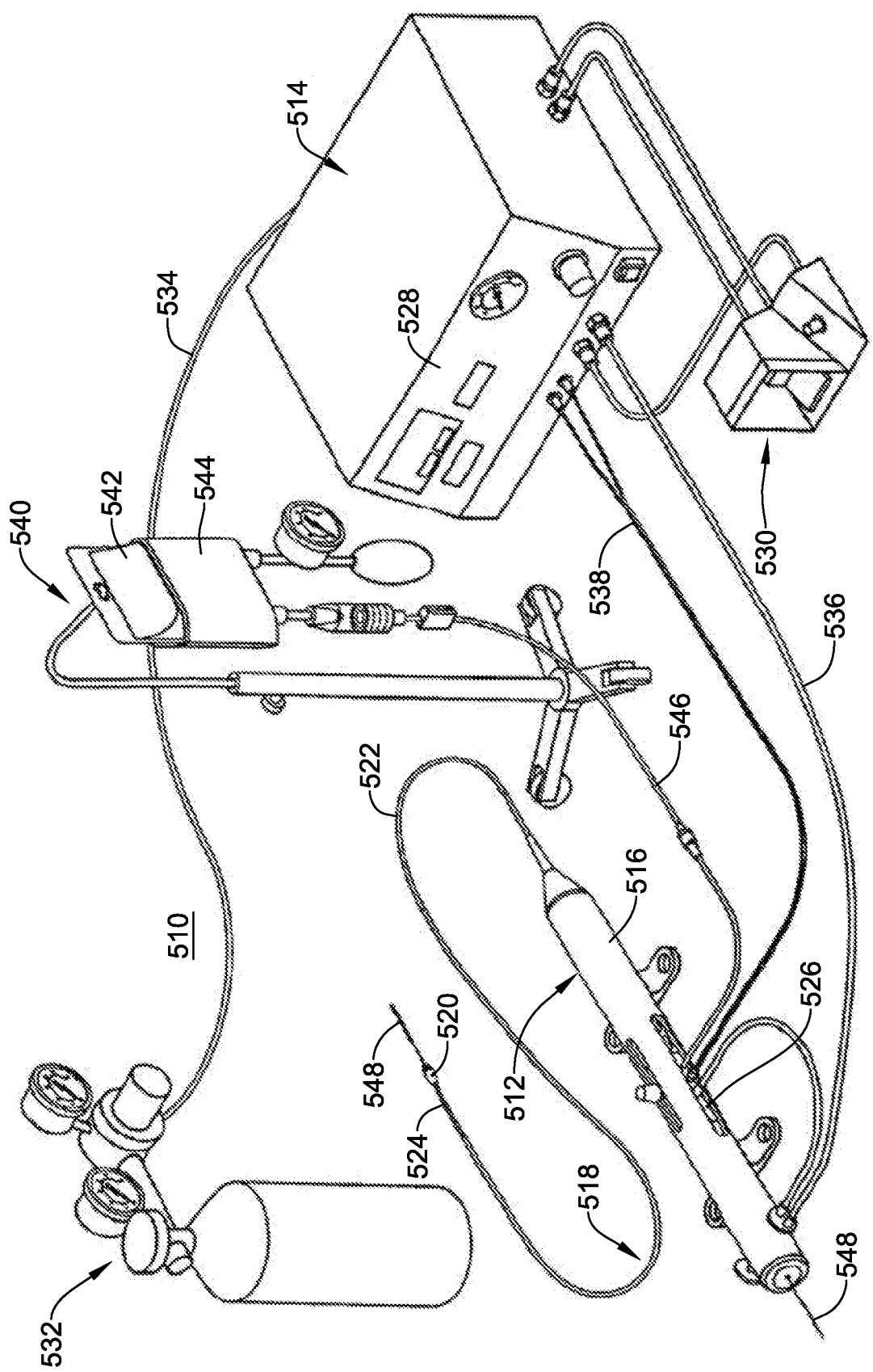
FIG. 7 is a schematic diagram of an example atherectomy system that may utilize the atherectomy control systems referenced in FIG. 1 through FIG. 4.

FIG. 7 shows an example rotational atherectomy system 510. The rotational atherectomy system 510 may include a rotational atherectomy device 512 and a controller 514 for controlling the rotational atherectomy device 512. The rotational atherectomy device 512 may include a housing 516 and an elongate shaft 518 extending distally from the housing 516 to a cutting member 520 located at a distal end of the elongate shaft 518. The elongate shaft 518 may include a drive shaft 524 to provide rotational motion to the cutting member 520. In some instances, the elongate shaft 518 may include an outer tubular member 522 having a lumen extending therethrough and the drive shaft 524 may extend through the lumen of the outer tubular member 522. The drive shaft 524, which may be fixed to the cutting member 520, may be rotatable relative to the outer tubular member 522 to rotate the cutting member 520. In some instances the axial position of the cutting member 520 relative to the outer tubular member 522 may be adjusted by moving the drive shaft 524 longitudinally relative to the outer tubular member 522. For example, the atherectomy device 512 may include an advancer assembly 526 positioned in the housing 516, or otherwise provided with the housing 516, that is longitudinally movable relative to the housing 516. The outer tubular member 522 may be coupled to the housing 516 while the drive shaft 524 may be coupled to the advancer assembly 526. Accordingly, the drive shaft 524 (and thus the cutting member 520) may be longitudinally movable relative to the outer tubular member 522 by actuating the advancer assembly 526 relative to the housing 516.

The rotational atherectomy device 512 may include a prime mover (not shown) to provide rotational motion to the drive shaft 524 to rotate the cutting member 520. For example, in some instances the prime mover may be a fluid turbine within the housing 516, such as provided with the advancer assembly 526. In other instances, however, the prime mover may be an electrical motor, or the like. The controller 514 may be used to control the prime mover. For example, the user may provide power to the prime mover and/or control the speed of rotation of the drive shaft 524 via the controller 514. For example, the front panel 528 of the controller 514 may include a user interface including a power switch, speed control mechanism (e.g., a speed control knob and/or buttons), a display, and/or other features for controlling the rotational atherectomy device 512. In some instances, the rotational atherectomy system 510 may include a remote control device 530, such as a foot pedal, a hand control, or other mechanism which may be used to control the power and/or speed to the prime mover, for example.

In instances in which the prime mover is an electric motor, the electric motor may be coupled to the controller 514 via an electrical connection to control the electric motor and/or provide electricity to the electric motor.

In some instances, the rotational atherectomy device 512 may include a speed sensor, such as an optical speed sensor, coupled to the controller 514 via a connector 538, such as a fiber optic connector to provide speed data to the controller 514. In other instances, an electronic sensor, such as a Hall Effect sensor, or other type of sensor may be used to sense the speed of the drive shaft 524 and cutting member 520. The speed data may be displayed, such as on the front panel 528 and/or the controller 514, and/or used to control the speed of the cutting member 520, such as maintaining a desired speed of the cutting member 520 during a medical procedure.

In some instances, the rotational atherectomy system 510 may be configured to infuse fluid through the elongate shaft 518 to the treatment site and/or aspirate fluid through the elongate shaft 518 from the treatment site. For example, the rotational atherectomy system 510 may include a fluid supply 540 for providing a flow of fluid through a lumen of the elongate shaft 518 to a treatment site. In some instances the fluid supply 540 may include a saline bag 542 which may be pressurized by a pressure cuff 544 to provide a pressurized fluid (e.g., saline) to the rotational atherectomy device 512 through a fluid supply line 546. In other instances, an infusion pump, such as a peristaltic pump, may be used to deliver pressurized fluid to the rotational atherectomy device 512. Additionally or alternatively, in some cases the rotational atherectomy system 510 may be configured to aspirate fluid from the treatment site. For example, the rotational atherectomy system 510 may include an aspiration pump, such as a peristaltic pump, to generate a vacuum to aspirate fluid through a lumen of the elongate shaft 518 to a fluid collection container (not shown), if desired.

In some instances, the elongate shaft 518 of the rotational atherectomy device 512 may be advanced over a guidewire 548 to a treatment site. For example, the drive shaft 524 may include a guidewire lumen through which the guidewire 548 may pass. Additionally or alternatively, the elongate shaft 518 may be advanced through a lumen of a guide catheter to a treatment site.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy system, comprising:
a handle;
a drive motor adapted to rotate a drive cable extending through the handle, the drive motor operably coupled to an atherectomy burr;
a control system adapted to regulate operation of the drive motor, the control system further adapted to:
provide the drive motor with a high frequency pulse width modulation (PWM) drive signal in order to operate the drive motor;
monitor a motor performance parameter;
add a low frequency PWM signal to the high frequency PWM drive signal when the motor performance parameter approaches a limit of a performance range, thereby causing the drive motor to produce a tactile signal that signals to the user that the motor performance parameter is approaching the limit of the performance range.

2. The atherectomy system of claim 1, wherein when the motor performance parameter crosses the limit of the performance range, the control system changes a frequency and/or amplitude of the low frequency PWM signal in order to make the tactile signal more noticeable.

3. The atherectomy system of claim 2, wherein after the motor performance parameter crosses the limit of the performance range to cause the control system to make the tactile signal more noticeable and the motor performance parameter further exceeds the limit of the performance range by a predetermined amount, the control system further changes the frequency and/or amplitude of the low frequency PWM signal in order to further increase an intensity of the tactile signal.

4. The atherectomy system of claim 1, wherein the tactile signal includes a vibration detectable in the handle by the user of the atherectomy system.

5. The atherectomy system of claim 1, wherein the tactile signal includes an audible buzz detectable by the user of the atherectomy system.

6. The atherectomy system of claim 1, wherein the motor performance parameter comprises a motor torque, and the control system is adapted to add the low frequency PWM signal to the high frequency PWM drive signal in response to the motor torque approaching or exceeding a predetermined torque value.

7. The atherectomy system of claim 1, wherein the motor performance parameter comprises a motor speed, and the control system is adapted to add the low frequency PWM signal to the high frequency PWM drive signal in response to the motor speed approaching or dropping below a predetermined speed value.

8. An atherectomy system, comprising:
a drive motor adapted to rotate a drive cable, the drive motor operably coupled to an atherectomy burr;
a control system adapted to regulate operation of the drive motor, the control system further adapted to:
provide the drive motor with a high frequency pulse width modulation (PWM) drive signal in order to operate the drive motor;
monitor a torque exerted by the drive motor;
monitor a speed of the drive motor;
add a low frequency PWM signal to the high frequency PWM drive signal when the torque approaches a torque threshold and/or when the speed approaches a speed threshold, thereby causing the drive motor to produce a tactile signal that signals to the user that the torque is approaching the torque threshold and/or the motor speed is approaching the speed threshold.

9. The atherectomy system of claim 8, wherein when the torque passes the torque threshold, the control system changes the amplitude and/or frequency of the low frequency PWM signal being added to the high frequency PWM drive signal in order to increase an intensity of the tactile signal in order to signal to the user that the torque is passing the torque threshold.

10. The atherectomy system of claim 8, wherein when the speed passes the speed threshold, the control system changes the amplitude and/or frequency of the low frequency PWM signal being added to the high frequency PWM drive signal in order to increase an intensity of the tactile signal in order to signal to the user that the speed is passing the speed threshold.

11. The atherectomy system of claim 8, wherein the control system is further adapted to alter a frequency and/or a magnitude of the low frequency PWM signal in response to how high the torque is relative to the torque threshold and/or how low the speed of the motor is relative to the speed threshold.

12. The atherectomy system of claim 8, wherein the control system is further adapted to maintain a safe level of torque at the atherectomy burr.

13. The atherectomy system of claim 8, wherein the control system is further adapted to maintain a speed at the atherectomy burr capable of rotating the atherectomy burr.

14. A control system for an atherectomy system including a drive motor adapted to rotate a drive cable, the drive motor operably coupled to an atherectomy burr, the control system comprising:
an input adapted to receive an indication of a motor performance parameter;
an output adapted to output a high frequency pulse width modulation (PWM) drive motor signal to the drive motor;
a controller operably coupled to the input and to the output, the controller adapted to provide to the output the high frequency PWM signal for operating the drive motor;
the controller further adapted, when the motor performance parameter approaches a limit of a performance range, to add a low frequency PWM signal to the high frequency PWM drive signal that is provided to the drive motor via the output, thereby causing the drive motor to produce a tactile signal that signals to the user that the motor performance parameter is approaching the limit of the performance range.

15. The control system of claim 14, wherein the motor performance parameter comprises motor torque.

16. The control system of claim 15, wherein when the motor torque passes a torque threshold, the controller changes an amplitude and/or a frequency of the low frequency PWM signal being added to the high frequency PWM drive signal in order to increase an intensity of the tactile signal in order to signal to the user that the torque is passing the torque threshold.

17. The control system of claim 16, wherein the controller is further adapted to further alter the amplitude and/or the frequency of the low frequency PWM signal in response to how high the torque is relative to the torque threshold.

18. The control system of claim 14, wherein the motor performance parameter comprises motor speed.

19. The control system of claim 18, wherein when the motor speed passes a motor speed threshold, the controller changes an amplitude and/or a frequency of the low frequency PWM signal being added to the high frequency PWM drive signal in order to increase an intensity of the tactile signal in order to signal to the user that the motor speed is passing the motor speed threshold.

20. The control system of claim 19, wherein the controller is further adapted to further alter the frequency and/or the magnitude of the low frequency PWM signal in response to how high the torque is relative to the torque threshold and/or how low the speed of the motor is relative to the speed threshold.

* * * * *